United States Patent [19]

Nappa et al.

[11] Patent Number: 4,960,951

[45] Date of Patent: Oct. 2, 1990

[54] NOVEL PERFLUOROPOLYETHERS

[75] Inventors: Mario J. Nappa, Newark; Allen C. Sievert, Elkton; Walter R. Tong, New Castle, all of Del.

[73] Assignee: E. I. Du Pont de Nemours and Company, Wilmington, Del.

[21] Appl. No.: 480,351

[22] Filed: Feb. 14, 1990

Related U.S. Application Data

[62] Division of Ser. No. 303,150, Jan. 30, 1989, abandoned.

[51] Int. Cl.$^5$ .............................................. C07C 43/12
[52] U.S. Cl. ...................... 568/615; 568/677; 568/606; 568/664; 568/669; 228/56.3; 252/54
[58] Field of Search .............. 568/615, 677, 606, 664, 568/669

[56] References Cited

U.S. PATENT DOCUMENTS

| | | | |
|---|---|---|---|
| 3,897,502 | 7/1975 | Russell et al. | 260/614 |
| 3,962,348 | 6/1976 | Benninger et al. | 568/677 |
| 4,510,335 | 6/1985 | Lagow et al. | 568/683 |
| 4,721,578 | 1/1988 | Dishart | 252/78.1 |
| 4,788,350 | 11/1988 | Lagow | 568/677 |

FOREIGN PATENT DOCUMENTS 1450467  9/1976  United Kingdom.

Primary Examiner—Howard T. Mars
Attorney, Agent, or Firm—Charles E. Krukiel

[57] ABSTRACT

Novel perfluoropolyethers, such as perfluorodipentaerythritol hexaethyl ether, and their intermediates exhibit excellent chemical and thermal stability and are useful as vapor phase soldering fluids and convection cooling liquids.

6 Claims, No Drawings

NOVEL PERFLUOROPOLYETHERS

This application is a division of application Ser. No. 07/303,150 filed Jan. 30, 1989.

BACKGROUND OF THE INVENTION

The present invention relates to the general class of perfluorinated compounds known as perfluoropolyethers and to their corresponding intermediates, which are fluoroalkyl ethers of polyhydric alcohols.

Perfluoropolyethers possess excellent chemical and thermal stability which ensures a wide field of application for these compounds as heat transfer media, sealing liquids, lubricants under extreme chemical conditions, additives for oils and greases, turbine propellents and hydraulic liquids. They exhibit low dielectric constants, high breakdown voltages and low loss factors in alternating fields which makes them particularly suited for applications in the electrical area. In the electronics industry, for example, perfluoropolyethers are particularly useful in vapor phase soldering or as convection cooling liquids in transformers or similar devices. Their excellent dissolving power for oxygen and carbon dioxide enables them to be used as oxygen conveyers in heart-lung machines and also directly as blood substitutes in living organisms. These products also find applications in many spheres of nuclear and chemical engineering. Because of their outstanding chemical resistance, they are superior to the polypropylene oxide fluids which hitherto dominated these application fields, especially at temperatures above 200° C.

Currently available vapor phase soldering fluids can be relatively expensive to manufacture, and they may release toxic vapors at their decomposition temperatures. In addition, some have a high solubility in soldering rosin which requires expensive reclamation and reduces fluid life. The compounds of this invention are generally superior in one or more of these respects.

Compositions disclosed in the art which most closely resemble the compounds of this invention are found in U.S. Pat. No. 3,692,348 and its British counterpart, GB 1,450,467. These two patents describe perfluoroethyl and perfluoropropyl ethers having the following formula:

$$(C_xF_{2x+1}OCF_2)_aR^f(OC_xF_{2x+1})_b$$

where $R^f = C_nF_{2n+2} - (a+b)$ n = 1–10
a,b = 0–4
with $a + b \geq 1$
x = 2, 3

Perfluoropentaerythritol tetraethyl ether and perfluoropentaerythritol tetrapropyl ether are examples of such compounds.

Both patents describe the synthesis of aliphatic and cyclic perfluoro-alkyl ethers in high yields in which tetrafluoroethylene or hexafluoropropene adducts of aliphatic or cyclic alcohols are subjected to electrofluorination.

SUMMARY OF THE INVENTION

The present invention relates to novel perfluoropolyether compounds which are represented by the following formulas (I), (II) and (III):

$$[(ROCF_2)_3CCF_2]_2O \quad (I)$$

$$[RO(R'')_xCF_2]_{4-y-z}CR'_y(CF_2OR)_z \quad (II)$$

$$[RO(R'')_xCF_2]_v\{CR'[O(R'')_xR]\}_e[CR'(OR)]_f(CF_2OR)_w \quad (III)$$

where $R = -C_2F_5, -C_3F_7, -CFCF_2CF_2CF_2$ 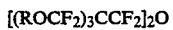

$R' = F, CF_3, C_2F_5$ $R'' = -CF_2CF_2O-, -CF(CF_3)CF_2O-, -CF_2CF(CF_3)O-$ x = 1, 2, 3
v, w = 0, 1, 2   v + w = 2
e, f = 0–4
$1 \leq e + f \leq 4$
y = 0, 1, 2
z = 0, 1, 2, 3, 4
with $(y + z) \leq 4$ Examples of the novel compounds of the invention are:
(a) Compounds of Formula (I)

$$(CF_3CF_2OCF_2)_3CCF_2OCF_2C(CF_2OCF_2CF_3)_3,$$

which is perfluoro-3,7,11-trioxa-5,5,9,9-tetrakis-(2'-oxabutyl)-tridecane.

(b) Compounds of Formula (II)

$$(CF_3CF_2OCF_2CF_2OCF_2)_2C(C_2F_5)CF_2OCF_2CF_3,$$

which is perfluoro-3,6,10,13-tetraoxa-8-(2'-oxabutyl)-8-ethyl-pentadecane, and its isomers, e.g., $$CF_3CF_2OCF_2CF_2OCF_2CF_2OCF_2C(C_2F_5)(CF_2OCF_2CF_3)_2$$

which is perfluoro-3,6,9,13-tetraoxa-11-(2'-oxabutyl)-11-ethyl-pentadecane;

$$[CF_3CF_2OCF(CF_3)CF_2OCF_2]_2C(CF_3)CF_2OCF_2CF_3$$

which is perfluoro-3,6,10,13-tetraoxa-8-(2'-oxabutyl)-4,8,12-trimethyl-pentadecane, and its isomers, e.g., $$[CF_3CF_2OCF_2CF(CF_3)OCF_2][CF_3CF_2OCF(CF_3)CF_2OCF_2]C(CF_3)-CF_2OC_2F_5,$$

which is perfluoro-3,6,10,13-tetraoxa-8-(2'-oxabutyl)-5,8,12-trimethyl-pentadecane;

(c) Compounds of Formula (III)

$$[CF_3CF_2OCF_2CF_2OCF_2]_2CFOCF_2CF_2OCF_2CF_3$$

which is perfluoro-3,6,10,13-tetraoxa-8-(3'-oxapentoxy)-pentadecane, and its isomers, e.g., $$C_2F_5OCF_2CF_2OCF_2CF_2OCF_2]CF(OC_2F_5)[CF_2OCF_2CF_2OC_2F_5],$$

which is perfluoro-3,6,9,13,16-pentaoxa-11-ethoxy-octadecane;

$$[CF_3CF_2OCF(CF_3)CF_2OCF_2]_2CFOCF_2CF_3$$

which is perfluoro-3,6,10,13-tetraoxa-8-ethoxy-4,12-dimethyl-pentadecane, and its isomers, e.g.,

C₂F₅OCF(CF₃)CF₂OCF(CF₃)CF₂OCF₂C-
F(OC₂F₅)CF₂OC₂F₅ which is perfluoro-3,6,9,13-tetraoxa-11-ethoxy-4,7,-dimethyl-pentadecane;

[CF₃CF₂OCF(CF₃)CF₂OCF₂]₂C(CF₃)₂ which is perfluoro-3 6 10 13-tetraoxa-4 8 8 12-tetramethyl-pentadecane, and its isomers, e.g.,

C₂F₅OCF₂CF(CF₃)OCF₂C(CF₃)₂C-
F₂OCF₂CF(CF₃)OC₂F₅, which is perfluoro-3,6,10,13-tetraoxa-5,8,8,12-tetramethyl-pentadecane; and

[CF₃CF₂CF₂OCF(CF₃)CF₂OCF₂]₂C(CF₃)₂ which is perfluoro-4,7,11,14-tetraoxa-5,9,9,132-tetramethyl-heptadecane, and its isomers, e.g.,

C₃F₇OCF(CF₃)CF₂OCF(CF₃)CF₂OCF₂C(CF₃)₂C-
F₂OC₃F₇ which is perfluoro-4,7,10,14-tetraoxa-5,2,12,12-tetramethyl-heptadecane.

The compounds of Formulas (I), (II) and (III) possess excellent chemical stability. They are thermally stable at high temperatures and extremely resistant to attack by oxygen, fluorine or other very aggressive chemicals. These properties make them particularly useful in the numerous applications previously described for perfluoropolyethers. The novel compounds of this invention are particularly effective as vapor phase soldering fluids. This is due to their narrow boiling point range, preferably less than 5° C. and most preferably less than 3° C., the boiling point range being between 180° C. and 280° C. and preferably between 210° C. and 275° C.

DETAILED DESCRIPTION OF THE INVENTION

The compounds of Formula (I) are prepared by a two-step photo-assisted solution phase direct fluorination process which is described in detail in U.S. patent application Ser. No.195,912, the teachings of which are incorporated herein by reference. The process comprises reacting a polyalcohol, i.e., a polyol, with a fluorinated olefin in the presence of a base in a polar aprotic solvent to form a partially fluorinated intermediate. The intermediate is dissolved in an inert solvent, and then an inert gas stream, which contains an initial fluorine concentration of from 1 to 10% by volume fluorine, is passed through the solution. The fluorine concentration is gradually increased according to a predetermined timed sequence, and the solution is irradiated with an ultraviolet source as and after the fluorine concentration in the gas stream reaches 20% by volume until the reaction is complete.

According to the present invention, for compounds of Formula (I) dipentaerythritol is the starting polyol. The perfluoro olefin which is reacted with the polyol in the first step is selected from the group comprising, tetrafluoroethylene, hexafluoropropylene, and hexafluorocyclobutene. Perfluorination of the intermediate, a hexaether, prepared in this manner is then conducted by photo-assisted solution phase direct fluorination.

The compounds of Formulas (II) and (III) are prepared according to the process described above, but an additional process step is required. This consists of a base-catalyzed alkoxylation of a polyhydridic, aliphatic alcohol with alkylene oxides of the formula:

$$\overline{OCH_2 CHR}, \text{ where } R = H, \text{ or } CH_3.$$

Alkoxylation reactions are conventional procedures for preparing polyethers, and the alkylene oxides can ordinarily be added directly to the polyol, using a stream of dry nitrogen as a carrier. The reaction is normally conducted at 120° C. to 170° C., but a temperature of 140° C. is preferred. It is advantageous to react polyols that are liquid at the reaction temperature, and it is preferred, from a convenience of handling standpoint, that the polyol have a melting point below 120° C. If the polyol to be used has a higher melting point, it can first be dissolved in a suitable solvent, such as a high-boiling polyether or a perfluoroolefin adduct of the alkoxylated product. Poly hydridic alcohols, also known as polyols, suitable for the process of the invention include 2,2-dimethyl-1,3-propanediol, 2-methyl-2-hydroxymethyl-1,3-propanediol, 2-ethyl-2-hydroxymethyl-1,3-propanediol, glycerol, erythritol, xylitol, sorbitol, mannose and related compounds:

The reaction must be conducted in a dry, oxygen-free system, and this is best accomplished by initially purging the equipment with nitrogen. A small quantity of sodium hydride is added to the polyol, typically 0.1 to 0.5% by weight, usually in the form of a hydrocarbon dispersion, such as 50% NaH in paraffin. This converts some of the polyol hydroxy groups to alkoxide groups which serve as a catalyst for the process as illustrated by the equation:

$$R(OH)_x + NaH = [R(OH)_{x-1}O]Na + H_2$$

At the conclusion of the alkoxylation of the polyol, sufficient acetic acid is added to neutralize the catalyst.

The average molecular weight of the products of this invention may be controlled by the amount of alkylene oxide that is reacted with the polyol. This can be monitored gravimetrically as the reaction proceeds.

However, since the alkoxylation process results in a distribution of polyols which is only partially controlled by the stoichiometry, it is desirable to vacuum distill the alkoxylated intermediates to obtain a narrow molecular weight distribution in the product. This is advantageous from an economic standpoint compared with fractionating the product after the final perfluorination step.

The reactivity of a molecule of alkylene oxide with a polyol is not highly site-selective. Hence, for a given molar ratio of alkylene oxide to polyol, a number of isomers can be produced. For example, 2 molar equivalents of ethylene oxide reacting with 2-ethyl-2-hydroxymethyl-1,3-propanediol would give a mixture of the following products:

C₂H₅C(CH₂OH)₂(CH₂OCH₂CH₂OCH₂CH₂OH)

and C₂H₅C(CH₂OH)(CH₂OCH₂CH₂OH)₂ as well as small amounts of compounds containing only one ethylene oxide unit and three or more ethylene oxide units.

In the case of propoxylation reactions, an additional possibility of isomer formation arises due to the presence of a methyl substituent in propylene oxide. Although it is known that base-catalyzed ring opening of propylene oxide normally gives the secondary alcohol, some of the primary alcohol will also be formed. For example, an alcohol, ROH, will react with propylene oxide to give predominantly $ROCH_2C(CH_3)HOH$ but some $ROC(CH_3)CH_2OH$ will also be formed. Surprisingly, formation of isomers such as these, and those described above, during the alkoxylation step is not detrimental to the final product because the boiling point of the perfluorinated mixture is normally within an acceptable range for typical inert fluid applications.

The alkoxylated products are then reacted with the perfluoroolefin as indicated above. The perfluoroolefin adducts of the alkoxylated polyols are then perfluorinated by photo-assisted solution phase direct fluorination.

The equation:

$$BP = -9.8(10)^{-5}(M)^2 + 0.38M - 54$$

where BP = the boiling point of the perfluoropolyether in °C, and

M = the molecular weight of the compound, may be used as an approximate guide for preparing perfluoropolyethers having a certain boiling point. The equation is only approximate and is not suited for compounds having $C_5$ or larger alkyl chains. Highly branched perfluoropolyethers often have somewhat higher boiling points than predicted by this equation.

Preferred vapor phase soldering fluids have molecular weights in the range of 883 to 1250 which corresponds to a range of boiling points of 205° C. to 268° C., as calculated using the above equation. The molecular weight of the compounds of this invention can be tailored to the desired value by an appropriate choice of the starting polyhydric alcohol and the perfluoro olefin. The molecular weight of the product may also be adjusted by ethoxylation or propoxylation of the polyhydridic alcohol prior to reaction with perfluoroolefin.

By way of illustration, reaction of 2-ethyl-2-hydroxymethyl-1,3-propandiol with 3 molar equivalents of tetrafluoroethylene affords the tris(1,1,2,2-tetrafluoroethyl) ether of the triol. Subsequent perfluorination of the partially fluorinated ether by photo-assisted solution phase direct fluorination affords F-2-ethyl-1,2,3-tris(ethoxy)propane having a boiling point of 162°-165° C. If the 2-ethyl-2-hydroxymethyl-1,3-propanediol is treated with 2 molar equivalents of ethylene oxide followed by vacuum distillation, a material having an overall composition corresponding to the bis(ethylene oxide) adduct of 2-ethyl-2-hydroxymethyl-1,3-propanediol is obtained. Reaction of this material with 3 molar equivalents of tetrafluoroethylene to give the tris(1,1,2,2-tetrafluoroethyl) ether followed by photo-assisted solution phase direct fluorination affords a mixture of perfluorinated compounds with a boiling point of 218°-220° C. (see Example 2).

EXAMPLE 1

Preparation of Perfluoro-3,7,11-trioxa-5,5,9,9-tetrakis(2'-oxabutyl)-tridecane

Step 1. Preparation of Dipentaerythritol Hexa(1,1,2,2-tetrafluoroethyl) Ether A 400 ml "Hastelloy" C bomb was charged with dipentaerythritol (21.19 g, 0.0833 mol), potassium hydroxide (9.35 g, 0.167 mol), and N,N-dimethylformamide (150 ml). The bomb was sealed, cooled to −78° C. in a dry ice-acetone bath, and purged three times with nitrogen. The bomb was then removed from the bath and secured in a reaction barricade. The bomb was agitated by shaking and then pressurized with 50 psig of tetrafluoroethylene (TFE). The pressure rapidly dropped; TFE was added in 50 psig increments until a total of 51.0 g had been added. The reactor was then warmed to 50° C. for 2 hours. The bomb was vented, purged with nitrogen, and the reaction mixture poured into a separatory funnel. The mixture was extracted with 150 ml of water and 75 ml of diethyl ether. The organic layer was washed two more times with water (100 ml) and then dried over anhydrous sodium sulfate. The ethereal extract was concentrated in vacuum and distilled (10 mm Hg). Three fractions were collected; the third fraction, collected at 203° C., weighed 32.1 g and was judged to be 91% pure dipentaerythritol hexa(1,1,2,2-tetrafluoroethyl) ether by gas chromatography (50% yield).

Step 2. Perfluorination of Dipentaerythritol Hexa(1,1,2,2-tetrafluoroethyl) Ether Dipentaerythritol hexa(1,1,2,2-tetrafluoroethyl ether (15.0 g, 17.56 mmol) was added to 350 ml of 1,1,2-trichlorotrifluoroethane (CFC-113) in an FEP reactor. The solution was cooled to -15° C. and purged with nitrogen for 0.5 hr. Fluorine diluted with nitrogen was added to reaction at the flow rates and for time periods indicated in the following schedule (the value in parentheses is the concentration of fluorine in the nitrogen carrier): 5.0 sccm (4.8%)-15 min., 12.0 sccm (13.8%) - 15 min., 25.0 sccm (33.3%) - 15 min., 35.0 sccm (50%) - 468 min., and 20.0 sccm (50%) - 80 min. The total ratio of fluorine to hydrogen atoms in the substrate was 1.71. When the fluorine concentration reached 28.6%, a UV flood lamp positioned adjacent to the reactor was turned on and irradiated the outside of the reactor body for the remainder of the experiment. Three 15 g reactions were run and the products from all three combined. The CFC-113 solution was washed with 5% sodium bicarbonate solution, 2 times with water, and dried with sodium sulfate. The liquid was rotary evaporated in vacuum to give 64.2 g of a cloudy oil, which was purified by vacuum distillation to give 51.7 g (66% yield) of perfluoro-3,7,11-trioxa-5,5,9,9-tetrakis(2'-oxabutyl)tridecane. The boiling point was 255-256° C.; the product was identified by elemental analysis, 19F NMR and GC-mass spectroscopy.

EXAMPLE 2

Preparation of Perfluoro-tris(ethyl ether) of 2-ethyl-2-hydroxymethyl1,3-propanediol bis(ethylene oxide) adduct

Step 1. Preparation of the Bis(ethylene oxide) Adduct of 2-Ethyl-2-hydroxymethyl-1,3-propanediol The triol was prepared by the reaction of ethylene oxide with neat 2-ethyl-2-hydroxymethyl-1,3-propanediol. A four-necked flask was fitted with a gas inlet tube, a gas outlet, a thermometer, and a mechanical stirrer. The gas inlet tube was connected to a cylinder of ethylene oxide with a nitrogen purge tee, a rotometer, a check valve, and a suck-back trap between the ethylene oxide cylinder and the gas inlet tube. The cylinder of ethylene oxide rested on an electronic balance. The reaction flask was charged with 200 g (1.49 mol) of 2-ethyl-2-hydroxymethyl-1,3-propanediol. The flask was placed in an electric heating mantle and the contents of the flask heated to 140° C. with a continuous purge of nitrogen through the gas inlet tube for 30 minutes with stirring to sparge out any water and oxygen in the reactor. The reaction flask was cooled to 100° C. Sodium hydride (0.4 g, 0.0083 mol, 50% dispersion in paraffin) was added to the flask, and the reaction was stirred for 30 minutes. The reaction was then reheated to 140° C. and 140 g (3.18 mol) of ethylene oxide was bubbled into the reaction over the course of about 2.5 hours. Nitrogen was co-fed with the ethylene oxide such that the volumetric ratio of nitrogen to ethylene oxide was about 1:1. At the conclusion of the addition, nitrogen was purged through the reaction and 0.89 g (0.015 mol) of acetic acid was added to neutralize the catalyst. 340 g of product were recovered.

325 g of the product were charged to a flask set up for a standard vacuum distillation. A forecut was collected at 70°-158° C. at a pressure of 3 mm Hg. This material was discarded. 131 g of product, amounting to a yield of 40.3%, was collected at 181°-194° C. at a pressure of 2 mm Hg. The pot residue was discarded. The 1H NMR spectrum of the product integrated correctly for a bis-(ethylene oxide) adduct of 2-ethyl-2-hydroxymethyl-1,3-propanediol as an average composition This material was used for reaction step 2.

Step 2. Preparation of the Tris[(1,1,2,2-tetrafluoro)ethyl ether] of 2-ethyl-hydroxymethyl-1,3propanediol-bis(ethylene oxide) adduct Bis(ethylene oxide) adduct of 2-ethyl-hydroxymethyl-1,3-propanediol (73.36 g, 0.33 mol), powdered potassium hydroxide (5.6 g, 0.1 mol), and N,N-dimethylformamide (100 ml, 94.4 g) were placed in a 400 ml "Hastelloy" C bomb. The bomb was sealed, cooled to −78° C., evacuated, and purged with nitrogen three times. The bomb was placed in a barricade, connected to a source of tetrafluoroethylene (TFE), and agitated by shaking. TFE was added to the bomb in 50 psig increments until 100 g (1.0 mol) had been added. During the course of the addition the temperature of the reaction increased to about 30.C. The temperature was increased to 50° C. and held at that temperature for 2 hours. The bomb was cooled, vented, and purged with nitrogen. The contents of the bomb were poured into a jar. The reaction mixture consisted of a clear, amber upper layer over a cloudy, white suspension in a lower layer. The weight of the mixture had increased by 103 g.

The reaction mixture was treated with 100 ml of water and the aqueous and organic layers separated. The yellowish organic layer was then dried over anhydrous sodium sulfate. The 1H NMR spectrum of the dried product was consistent with that of a tris(tetrafluoroethylene) adduct of the starting triol. The product had a Brookfield viscosity of 35 cp at ambient temperature; the density was 1.378 g/ml.

The product was then distilled at 15 mm Hg to afford four fractions with the following boiling point ranges: 140°-162° C. (17.06 g), 162°-178° C. (51.69 g), 178°-180° C. (54.11 g), 170° C. (10.67 g). The pot residue, which was discarded, weighed 1.68 g. The 1H NMR analysis of the four fractions suggested than on average each fraction contained 0.65, 1.35, 2.25 and 3.0 ethylene oxide units, respectively, per unit of 2-ethyl-2-hydroxymethyl-1,3-propanediol. This corresponds to a 77% yield of distillable material. The third fraction was used for the next step.

Step 3. Perfluorination of the Tris[(1,1,2,2-tetrafluoro)ethyl ether] of 2-ethyl-hydroxymethyl-1,3-propanediol-bis(ethylene oxide) adduct Tris(1,1,2,2-tetrafluoro)ethyl ether of the bis(ethylene oxide) adduct of 2-ethyl-hydroxymethyl-1,3-propanediol (5.0 g, 9.57 mmol) was added to CFC-113 (370 ml) in an FEP reactor. The solution was cooled to −15° C. and purged with nitrogen at 100 sccm for half an hour. Fluorine diluted with nitrogen was added to the reaction at flow rates and for the time periods indicated in the following schedule (the values in parentheses are the volume percentages of fluorine in the nitrogen carrier): 5 sccm (4.8%) - 20 min., 10 sccm (11.8%) - 20 min., 20 sccm (28.6%) - 20 min., 20 sccm (40%) - 20 min., and 20 sccm (50%) - 326 min. When the $F_2$ concentration in the nitrogen reached 28.6%, a UV flood lamp positioned outside the reactor body and directed at the reaction mixture, was turned on for the remainder of the experiment. At the end of the reaction, the molar ratio of fluorine to hydrogen in the substrate was 1.5. The perfluorinated product was isolated by vacuum distillation (7.77g, yield 49%). The boiling point was 218°-220° C.

We claim:
1. A compound of the formula

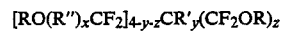

where R is $-C_2F_5$, $-C_3F_7$, or $-CFCF_2CF_2CF_2$:
R' is F, $CF_3$, or $C_2F_5$;
R''$-CF_2CF_2O-$, $-CF(CF_3)CF_2)O-$ or $-CF_2CF(CF_3)O-$;
x is 1, 2, or 3;
y is 0, 1, or 2; and
z is 0, 1, 2, 3, or 4; with the proviso that [(x+y)] (y+z)≦4.

2. The compound of claim 1 which is perfluoro-3,6,10,13-tetraoxa-8-(2'-oxabutyl)-8-ethylpentadecane and its isomers.

3. The compound of claim 1 which is perfluoro-3,6,9,13-tetraoxa-11-(2'-oxabutyl-11-ethylpentadecane and its isomers.

4. The compound of claim 1 which is perfluoro-3,6,10,13-tetraoxa-8-(2'-oxabutyl)-4,8,12-trimethyl-pentadecane and its isomers.

5. The compound of claim 1 which is perfluoro-3,6,10,13-tetraoxa-4,8,8,12-tetramethylpentadecane and its isomers.

6. The compound of claim 1 which is perfluoro-4,7,11,14,-tetraoxa-6,9,9,12-tetramethylheptadecane and its isomers.

* * * * *